(12) United States Patent
Fu

(10) Patent No.: US 10,716,705 B2
(45) Date of Patent: Jul. 21, 2020

(54) SYSTEMS AND METHODS FOR FEMTOSECOND LASER PHOTOREFRACTIVE KERATECTOMY

(71) Applicant: AMO Development, LLC, Santa Ana, CA (US)

(72) Inventor: Hong Fu, Pleasanton, CA (US)

(73) Assignee: AMO Development, LLC, Santa Ana, CA (US)

( * ) Notice: Subject to any disclaimer, the term of this patent is extended or adjusted under 35 U.S.C. 154(b) by 730 days.

(21) Appl. No.: 14/968,618

(22) Filed: Dec. 14, 2015

(65) Prior Publication Data

US 2016/0250074 A1   Sep. 1, 2016

Related U.S. Application Data

(60) Provisional application No. 62/121,241, filed on Feb. 26, 2015.

(51) Int. Cl.
*A61B 18/20* (2006.01)
*A61F 9/008* (2006.01)
*A61F 9/009* (2006.01)

(52) U.S. Cl.
CPC .......... *A61F 9/00814* (2013.01); *A61F 9/009* (2013.01); *A61F 9/00808* (2013.01); *A61F 9/00827* (2013.01); *A61F 9/00836* (2013.01); *A61F 9/00838* (2013.01);
(Continued)

(58) Field of Classification Search
CPC ...... A61F 9/007; A61F 9/008; A61F 9/00802; A61F 9/00804; A61F 9/00806; A61F 9/00814; A61F 9/00825; A61F 9/00827; A61F 9/00829; A61F 9/0084;
(Continued)

(56) References Cited

U.S. PATENT DOCUMENTS

| 4,665,913 A | 5/1987 | L'esperance, Jr. |
| 4,669,466 A | 6/1987 | L'esperance |
| 4,732,148 A | 3/1988 | L'esperance, Jr. |

(Continued)

FOREIGN PATENT DOCUMENTS

| CA | 2127029 C | 8/2003 |
| EP | 1787607 A1 | 5/2007 |

(Continued)

OTHER PUBLICATIONS

International Search Report and Written Opinion for Application No. PCT/US2015/065622, dated Mar. 17, 2016, 15 pages.
(Continued)

*Primary Examiner* — Ahmed M Farah
(74) *Attorney, Agent, or Firm* — Johnson & Johnson Surgical Vision, Inc.

(57) ABSTRACT

Embodiments of this invention generally relate to ophthalmic laser procedures and, more particularly, to systems and methods for photorefractive keratectomy. In an embodiment, an ophthalmic surgical laser system comprises a laser source generating a pulsed laser beam and a laser delivery system delivering the pulsed laser beam to a cornea of an eye. A patient interface couples to and constrains the eye relative to the laser delivery system. A controller controls the laser delivery system to perform an anterior surface volume dissection on the cornea.

11 Claims, 11 Drawing Sheets

(52) U.S. Cl.
CPC ............... *A61F 2009/00872* (2013.01); *A61F 2009/00895* (2013.01); *A61F 2009/00897* (2013.01)

(58) Field of Classification Search
CPC .. A61F 2009/00861; A61F 2009/00872; A61F 2009/00897
USPC ............................................ 606/3–6, 10–12
See application file for complete search history.

(56) References Cited

U.S. PATENT DOCUMENTS

| | | | |
|---|---|---|---|
| 4,764,930 A | 8/1988 | Bille et al. | |
| 4,770,172 A | 9/1988 | L'esperance, Jr. | |
| 4,773,414 A | 9/1988 | L'esperance, Jr. | |
| 5,108,388 A | 4/1992 | Trokel et al. | |
| 5,163,934 A | 11/1992 | Munnerlyn | |
| 5,207,668 A | 5/1993 | L'esperance, Jr. | |
| 5,219,343 A | 6/1993 | L'esperance, Jr. | |
| 5,646,791 A | 7/1997 | Glockler | |
| 5,993,438 A | 11/1999 | Juhasz et al. | |
| 6,315,413 B1 | 11/2001 | Shimmick et al. | |
| 6,325,792 B1* | 12/2001 | Swinger ............... | A61F 9/00804 606/11 |
| 8,171,937 B2* | 5/2012 | Bendett ............... | A61F 9/00827 128/898 |
| 8,260,024 B2 | 9/2012 | Farrer et al. | |
| 8,394,084 B2 | 3/2013 | Blumenkranz et al. | |
| 8,403,921 B2 | 3/2013 | Blumenkranz et al. | |
| 8,496,651 B2 | 7/2013 | Ruiz et al. | |
| 8,690,862 B2 | 4/2014 | Palanker et al. | |
| 8,709,001 B2 | 4/2014 | Blumenkranz et al. | |
| 10,369,052 B2* | 8/2019 | Fu ....................... | A61F 9/00834 |
| 10,369,053 B2* | 8/2019 | Srinivasan .......... | A61F 9/00834 |
| 2005/0107773 A1* | 5/2005 | Bergt ................... | B23K 26/08 606/4 |
| 2008/0058781 A1* | 3/2008 | Langeweyde ....... | A61F 9/00806 606/5 |
| 2009/0118718 A1 | 5/2009 | Raksi et al. | |
| 2009/0275929 A1* | 11/2009 | Zickler ................. | A61B 3/113 606/5 |
| 2011/0172649 A1 | 7/2011 | Schuele et al. | |
| 2013/0155375 A1 | 6/2013 | Rathjen et al. | |
| 2014/0104576 A1 | 4/2014 | Bor et al. | |
| 2014/0236135 A1 | 8/2014 | Donitzky et al. | |
| 2016/0346118 A1* | 12/2016 | Sluyterman van Langeweyde ..... | A61F 9/00806 |
| 2019/0021908 A1* | 1/2019 | Scott ................... | A61F 9/00827 |
| 2019/0125584 A1* | 5/2019 | Chernyak ............ | A61F 9/00827 |

FOREIGN PATENT DOCUMENTS

| | | |
|---|---|---|
| EP | 2596775 A1 | 5/2013 |
| WO | 9409849 A1 | 5/1994 |
| WO | 2008030699 A2 | 3/2008 |
| WO | 2012170966 A1 | 12/2012 |

OTHER PUBLICATIONS

Da Shiple., and J Aquavella., "A Review of Surgical Advancements for the Correction of Presbyopia," Expert Review of Ophthalmology, 2014, vol. 9(1), pp. 43-48.

Vestergaard A.H., "Past and Present of Corneal Refractive Surgery," Acta Ophthalmologica, 2014, vol. 92(2), pp. 1-21.

* cited by examiner

SYSTEMS AND METHODS FOR FEMTOSECOND LASER PHOTOREFRACTIVE KERATECTOMY

CROSS-REFERENCE TO RELATED APPLICATIONS

This application is a non-provisional application and claims the benefit under 35 U.S.C. § 119(e) of U.S. Provisional Application Ser. No. 62/121,241, filed Feb. 26, 2015, which is incorporated herein in its entirety by reference.

The subject matter of this disclosure is related to U.S. Patent App. Ser. No. 62/055,437, filed Sep. 25, 2014, entitled "SYSTEMS AND METHODS FOR LENTICULAR LASER INCISION," the entire disclosure of which is incorporated herein by reference and suitable for combination according to the embodiments disclosed here.

FIELD OF THE INVENTION

Embodiments of this invention relate generally to laser-assisted ophthalmic procedures, and more particularly, to systems and methods for photorefractive keratectomy (PRK).

BACKGROUND OF THE INVENTION

Many patients have visual errors associated with the refractive properties of the eye such as nearsightedness (myopia), farsightedness (hyperopia) and astigmatism. Nearsightedness can occur when light focuses before the retina, and farsightedness can occur with light refracted to a focus behind the retina. Astigmatism may occur when the corneal curvature is unequal in two or more directions. These visual impairments are commonly corrected using eyeglasses or contact lenses.

Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. With recent developments in laser technology, laser surgery is becoming the technique of choice for ophthalmic procedures. The reason many eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser System, the IntraLase FS Laser System, and OptiMedica's Catalys Precision Laser System.

Prior surgical approaches for reshaping the cornea include laser assisted in sine keratomileusis (hereinafter "LASIK"), photorefractive keratectomy (hereinafter "PRK") and Small Incision Lens Extraction (hereinafter "SmILE,").

LASIK and PRK are currently the two most commonly performed myopia correction procedures. In the LASIK procedure, an ultra-short pulsed laser is used to cut a conical flap that is folded open to expose the corneal stroma for photoablation with ultraviolet beams from an excimer laser. Photoablation of the cortical stroma reshapes the cornea and corrects the refractive condition such as myopia, hyperopia, astigmatism, and the like. After the corneal stroma has been photoablated with the excimer laser, the corneal flap is folded back and closed.

LASIK has the advantages of providing nearly immediate improvement in vision with a minimal amount of pain. There are, however, some disadvantages. Because a void is often created under the flap, the reshaped cornea is structurally weaker after surgery. To address this, LASIK to candidates are typically limited to those patients who have corneas that are about 500-600 µm thick. Further, LASIK requires an ultra-short pulsed laser to cut the cortical flap and a separate excimer laser to ablate the corneal stroma. As would be expected, requiring multiple laser systems increases costs and requires bigger storage areas for the equipment.

It is known that if part of the cornea is removed, the pressure exerted on the cornea by the aqueous humor in the anterior chamber of the eye will act to close the void created in the cornea, resulting in a reshaped cornea. By properly selecting the size, shape and location of a corneal void, one can obtain the desired shape, and hence, the desired optical properties of the cornea.

Hence, recently surgeons have started using another surgical technique for refractive correction. Instead of ablating corneal tissue with an excimer laser following the creation of a corneal flap, the newer technique involves tissue removal with two femtosecond laser incisions that intersect to create a lenticule for extraction. Lenticular extractions can be performed either with or without the creation of a corneal flap. With the flapless procedure, a refractive lenticule is created in the intact portion of the anterior cornea and removed through a small incision. In a SmILE procedure, as shown in FIG. 10, a femtosecond laser is used to make a side cut 1010, upper surface cut 1020 and lower surface cut 1030. A tweezer, for example, is then used to extract the cut lens 1040 beneath the anterior surface of the cornea 1000 through the side cut 1010.

PRK is another alternative to the LASIK procedure. In the PRK procedure, an excimer laser is used to directly remove material from a cornea without creating a flap. First, an epithelium layer of the cornea is removed prior to laser ablation. The epithelium layer will regrow within a few days after the procedure. As shown in FIG. 11, an initial cornea shape 1100 is reshaped by an excimer laser. Based on a desired myopic correction, a small amount of thin-lens shaped cornea stroma tissue 1110 is removed from the anterior cornea by photoablation. After material removal, the anterior cornea stroma will not regrow, thus resulting in a permanent shape change in the anterior cornea 1120.

Currently, all PRK procedures use an excimer laser to ablate and remove the anterior corneal stroma tissue, PRK provides vision correction with higher corneal mechanical strength than LARK does since there is no flap, and hence, no resulting void created underneath the flap. PRK is typically recommended for patients with thin corneas with a thickness under about 500 µm. PRK is, however, generally considered a more painful procedure with a typical recovery time of two weeks.

At least some prior ophthalmic laser surgery systems can be less than ideal in some instances. For example, prior laser surgery systems for performing a PRK procedure require an excimer laser because of its ability to accurately remove small amounts of corneal tissue. Tissue ablation rates with an excimer laser, however, can vary with the level of corneal hydration. And, to perform LASIK, SmILE, and PRK procedures, both a femtosecond laser surgery system and an excimer laser system are needed, thereby increasing costs.

For all these reasons, improved methods and systems that overcome at least some of the above limitations of prior systems and methods are desired.

SUMMARY OF THE INVENTION

Hence, to obviate one or more problems due to limitations or disadvantages of the related art, this disclosure provides embodiments for improved systems and methods that provide an improved PRK procedure using a femtosecond laser, including for example, an ophthalmic surgical laser system including a laser source generating a pulsed laser beam and a laser delivery system delivering the pulsed laser beam to a cornea of an eye. Embodiments also include a patient interface for coupling to and constraining the eye relative to the laser delivery system. A controller controls the laser delivery system to perform an anterior surface volume dissection on the cornea. This dissection allows removal of a portion of corneal tissue containing the anterior corneal surface.

The embodiments described here provide improved treatment of materials such as tissue. In many embodiments the tissue comprises ocular tissue such as one or more of corneal tissues that are incised for refractive surgery. Further, in many embodiments, improved methods and apparatus for performing laser eye surgery are provided for beneficially reshaping tissue structures of the eye to correct distortions in vision.

In some variations, the laser source may be an ultra-short pulsed laser such as a femtosecond laser. In other embodiments, the laser source may be a 355 nm ultraviolet (UV) laser. A surface of the patient interface in contact with the cornea may either be flat, curved, or may include a liquid or gel interface. The laser delivery system may scan the cornea by point-to-point scanning or by fast scan line scanning. A depth of focus of the pulsed laser beam may be under 10 μm and may be given by:

$$\Delta = \frac{0.905 \cdot \lambda}{(NA)^2},$$

where λ is a laser wavelength and NA is a numerical aperture.

Another aspect of the disclosure provides a method for correcting vision in an eye using an ophthalmic surgical laser system including the steps of coupling the eye to a patient interface to constrain the eye relative to the system, generating a pulsed laser beam or an ultraviolet beam with a laser source, and using a laser delivery system to deliver the beam to the cornea of the eye. A controller controls the laser delivery system to perform an anterior surface volume dissection in the cornea.

In some variations, the controller controls the anterior surface volume dissection to correct myopia, hyperopia, presbyopia, or astigmatism.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF THE PREFERRED EMBODIMENTS

The following description describes various embodiments of the present invention. For purposes of explanation, specific configurations and details are set forth so as to provide a thorough understanding of the embodiments. It will also, however, be apparent to one of ordinary skill in the art that embodiments of the present invention can be practiced without certain specific details. Further, to avoid obscuring the embodiment being described, various well-known features may be omitted or simplified in the description.

Embodiments of this invention are generally directed to systems and methods for laser-assisted ophthalmic procedures, and more particularly, to systems and methods for a PRK procedure performed using an ultra-short pulsed laser source such as a femtosecond laser. In certain embodiments, the laser source may be a 355 nm ultraviolet (UV) laser.

The embodiments disclosed herein are well suited for combination with prior laser surgery systems, such as Abbott Medical Optics Inc.'s iFS Advanced Femtosecond Laser System, the IntraLase FS Laser System, and OptiMedica's Catalys Precision Laser System. These systems can be modified according to the teachings disclosed here so as to more accurately treat the eye.

The embodiments disclosed herein are also suited for combination with corneal measurement systems. The corneal measurement system may comprise a component of the laser surgery system. The patient's cornea may be measured while the patient is lying on a patient bed that may be a part of the laser surgery system. Alternatively, the corneal measurement system may comprise a corneal measurement system that is separate from the laser system, and located in another area of another room of the physician's office, or surgical center.

As used herein, the terms anterior and posterior refer to known orientations with respect to the patient. Depending on the orientation of the patient for surgery, the terms anterior and posterior may be similar to the terms upper and lower, respectively, such as when the patient is placed in a supine position on a bed. A person of ordinary skill in the art will recognize many variations of the orientation of the methods and apparatus as described herein, and the terms anterior, posterior, upper, and lower are used merely by way of example.

Figure 1:
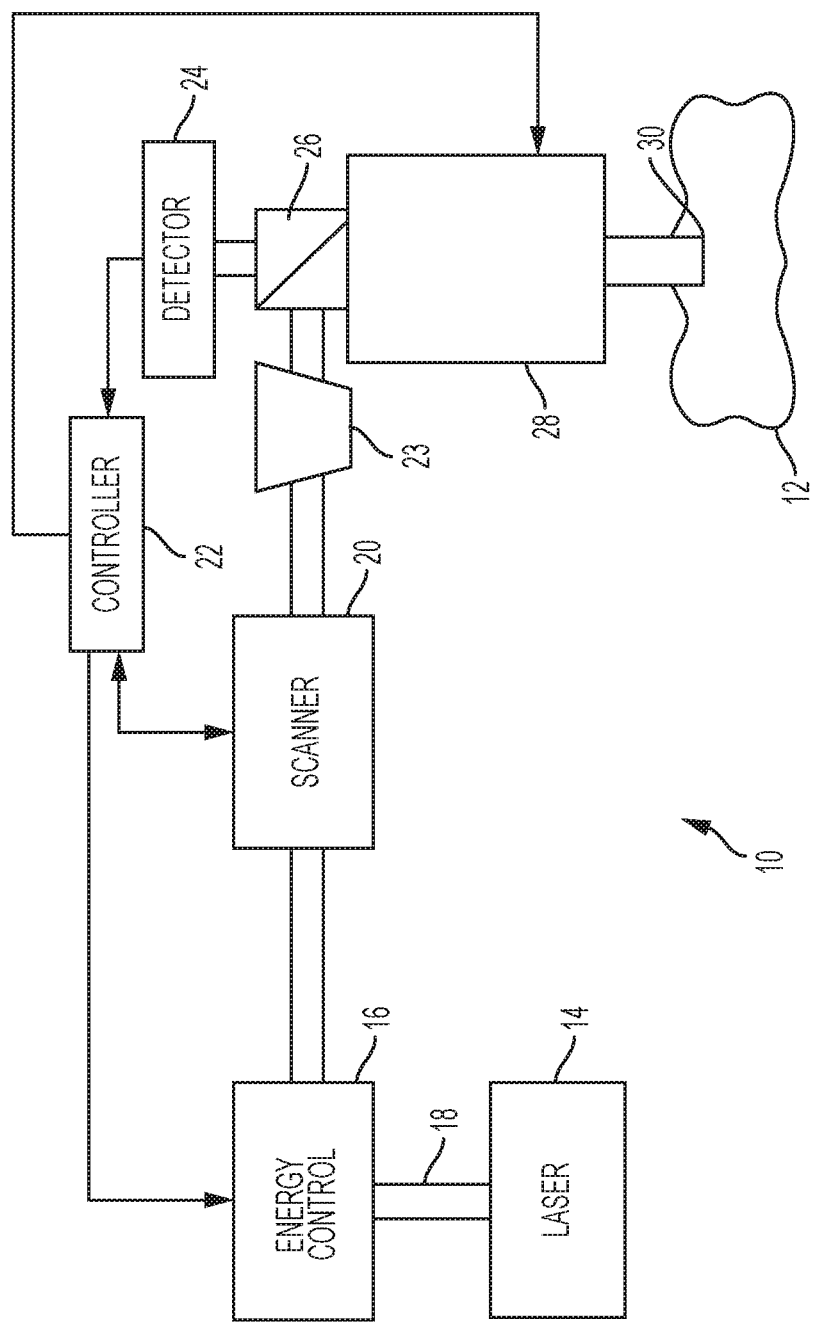
FIG. 1 is a perspective view of a surgical ophthalmic laser system according to an embodiment of the present invention.

Referring to the drawings, FIG. 1 shows a system 10 for making a surface volume dissection in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulsed laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to a position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from a surface volume monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a surface volume dissection in response to the feedback, and may also modify the planned dissection based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

In some embodiments, laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material and form three-dimensional removable structures of the material, and the like. The term "scan" or "scanning" refers to the movement of the focal point of the pulsed laser beam along a desired path or in a desired pattern.

An exemplary set of laser parameters for the femtosecond laser may include a pulse duration (width) of 50 femtosecond to 10 picosecond, a pulse frequency of 10 KHz to 20 MHz, wavelength of 100 nm to 2000 nm (e.g., 1030 nm to 1064 nm), and a pulse energy of 50 nanojoule to 5 microjoule.

In other embodiments, the laser 14 may comprise a laser source configured to deliver an ultraviolet (UV) laser beam comprising a plurality of ultraviolet laser pulses capable of photodecomposing one or more intraocular targets within the eye. An exemplary net of laser parameters for the UV laser may include a 355 nm laser with a pulse duration width) of 100 picosecond to 5 nanosecond (0.7 ns), a pulse frequency of 10 KHz to 500 KHz, a wavelength of 355 nm, and a pulse energy of 160 nanojoule to 5 microjoule.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for surface volume dissection of superficial tissue. In these embodiments, the surgical laser system 10 may also include a patient interface contacting the eye to change the shape of the cornea (for example, flatten or curve) prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 2:
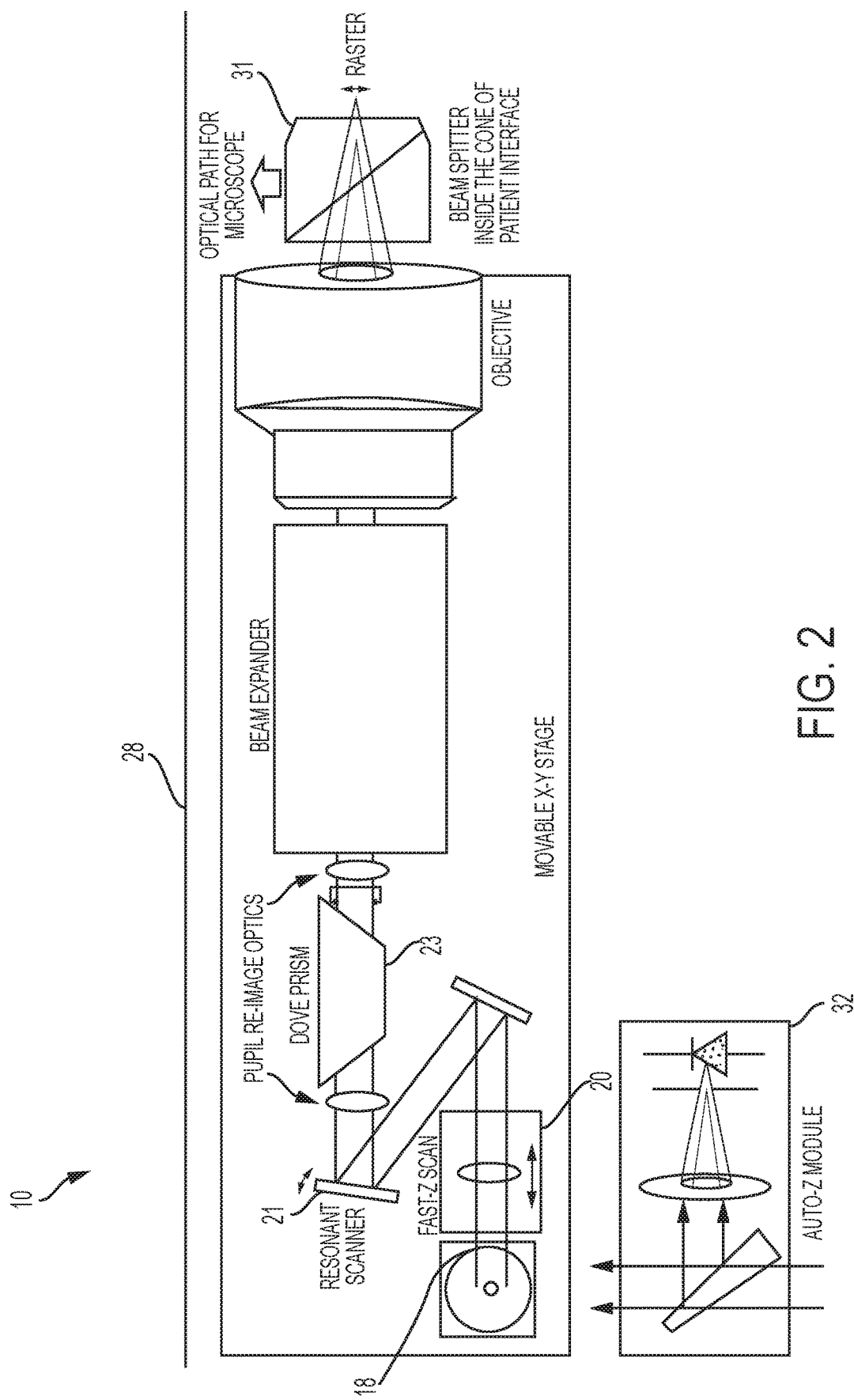
FIG. 2 is another perspective view of a surgical ophthalmic laser system according to an embodiment of the present invention.

FIG. 2 shows another exemplary diagram of the laser system 10. FIG. 2 shows components of a laser delivery system including a moveable XY-scanner (or XY-stage) 28 of a miniaturized femtosecond laser system. In this embodiment, the system 10 uses a femtosecond oscillator, comprising a fiber oscillator-based low energy laser. This allows the laser to be made much smaller. The laser-tissue interaction is in the low-density-plasma mode. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. The patient interface 31 is used to restrain the position of the patient's eye 43 relative to the system 10. The portion of the patient interface 31 that engages the eye may be flat or curved, as discussed in greater detail with respect to FIGS. 7 and 8. The flat patient interface includes a flat posterior surface in contact with the cornea to couple and constrain the eye relative to the system 10. Likewise, the curved patient interface includes a curved posterior surface in contact with the cornea to couple and constrain the eye relative to the system 10. The patient interface 31 assembly can be configured to demountably couple with the system 10 to enable replacement of the patient interface between treatments. The patient interface assembly can include, for example, a removable assembly, an interchangeable assembly, and/or an exchangeable assembly.

In some embodiments, a liquid interface is used between a patient interface lens and the eye. The use of the liquid interface prevents imparting undesirable forces to the patient's eye. The patient interface 31 may employ a suction ring that is vacuum attached to the patient's eye. The suction ring is then coupled with the patient interface 31, for example, using vacuum to secure the suction ring to the patient interface 31. In many embodiments, the patient interface 31 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) disposed between and in contact with the patient interface lens posterior surface and the patient's cornea.

A beam splitter is placed inside the cone of the patient interface to allow the whole eye to be imaged via visualization optics. In one embodiment, the system 10 uses: optics with a 0.6 numerical aperture (NA) which would produce 1.1 μm Full Width at Half Maximum (FWHM) focus spot size; and a resonant scanner 21 that produces 1-2 mm scan line with the XY-scanner scanning the resonant scan line to a 1.0 mm field. The prism 23 rotates the resonant scan line in any direction on the XY plane. The fast-Z scanner 20 sets the incision depth. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while he or she is lying down. Alternatively, the system 10 may be a UV laser system.

Figure 3:
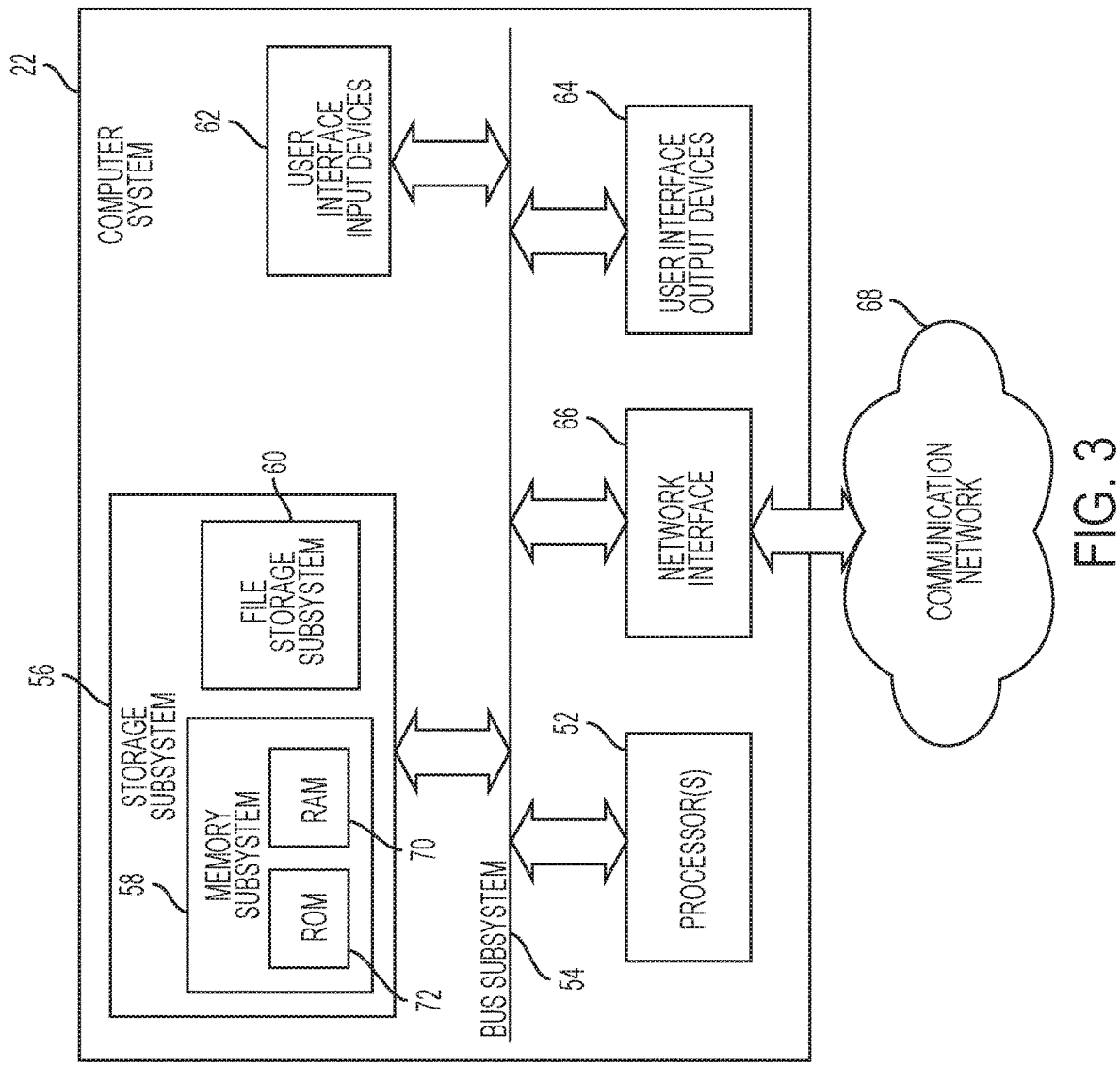
FIG. 3 is a simplified diagram of a controller of a surgical ophthalmic laser system according to an embodiment of the present invention.

FIG. 3 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54 to control the laser system 10 and execute at least some of the steps discussed in detail below. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive. DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging system or alignment system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In some embodiments, the laser surgery system 10 includes a femtosecond oscillator-based laser operating in the MHz range, for example, 10 MHz, or from several MHz to 500 MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing Objective, or one or more lenses within the focusing objective, along the optical axis. It is noted that in many embodiments, the XY-scanner 28 deflects the pulse laser beam 18 to form a scan line. This is otherwise referred to as point-to-point scanning.

Figure 4:
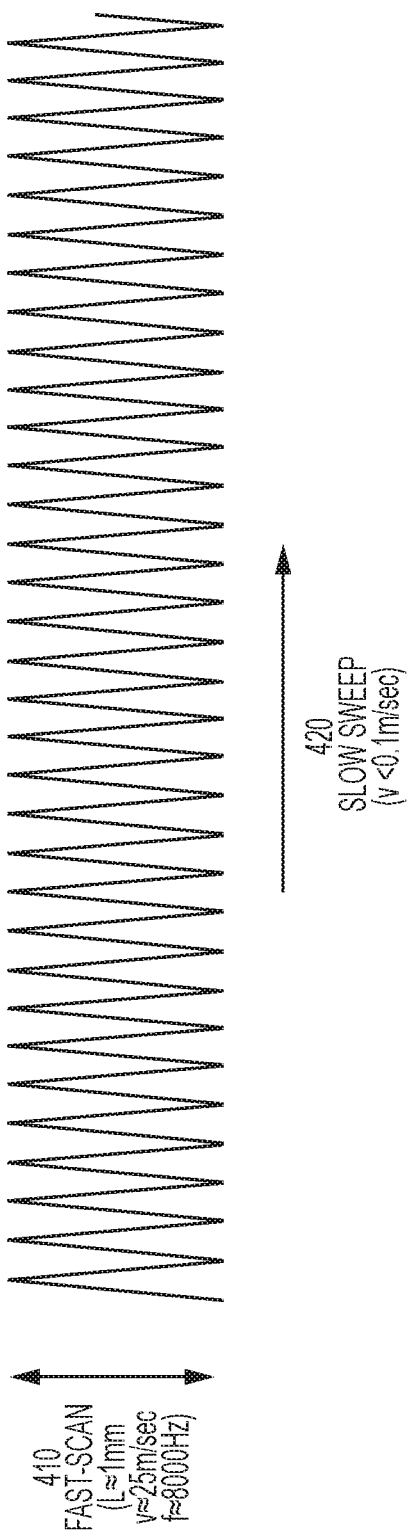
FIG. 4 illustrates an exemplary scanning of a surgical ophthalmic laser system according to an embodiment of the present invention.

In other embodiments, the beam scanning can be realized with a fast-scan-slow-sweep scanning scheme, also referred herein as a fast-scan line scheme. The scheme consists of two scanning mechanisms: first, a high frequency fast scanner is used to produce a short, fast scan line (e.g., a resonant scanner 21 of FIG. 2); second, the fast scan line is slowly swept by the much slower X, Y, and Z scan mechanisms. FIG. 4 illustrates a scanning example of a laser system 10 using an 8 kHz resonant scanner 21 to produce a fast scan line 410 of about 1 mm and a scan speed of about 25 m/sec, and X, Y, and Z scan mechanisms with the scan speed smaller than 0.11 m/sec. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e. XY-scanner 28 and Z-scanner 20). An advantage of the fast-scan-slow-sweep scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
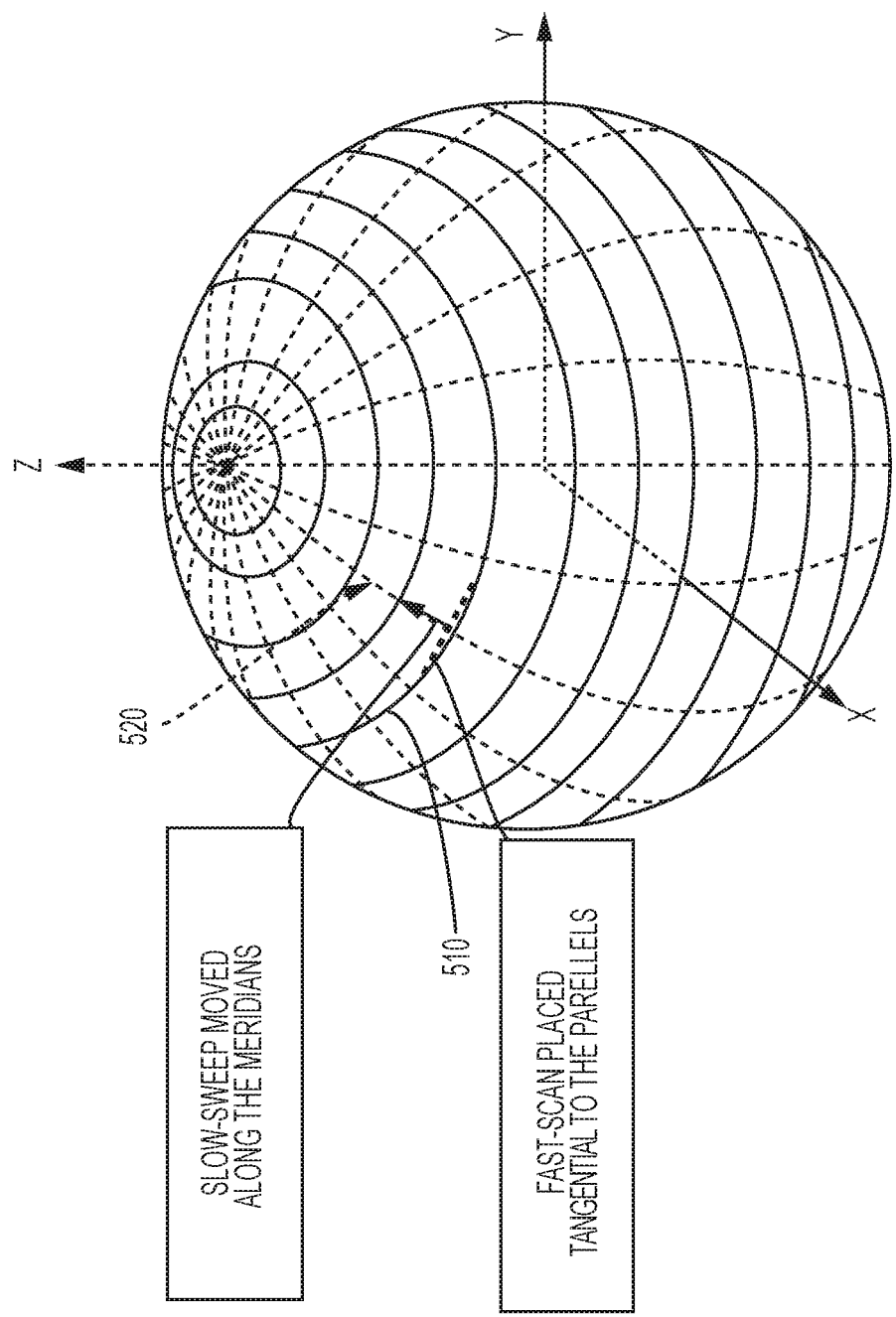
FIG. 5 illustrates an exemplary surface dissection using a fast-scan-slow-sweep scheme of a surgical ophthalmic laser system according to an embodiment of the present invention.

In another embodiment shown in FIG. 5, the laser system 10 creates a smooth surface dissection using the fast-scan-slow-sweep scanning scheme under an exemplary procedure. First, in a three-dimensional surface volume dissection, the fast scan line is preferably placed tangential to the parallels of latitude 510. For example, in the miniaturized flap maker laser system 10 of FIG. 2, this can be realized by adjusting a prism 23 to the corresponding orientations via software, e.g., via the controller 22. Second, the slow sweep trajectory preferably moves along the meridians of longitude 520. For example, in the miniaturized flap maker system of FIG. 2, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter. With this preferred procedure, there are no vertical "steps" in the dissection, and vertical side cuts are eliminated.

Figure 6:
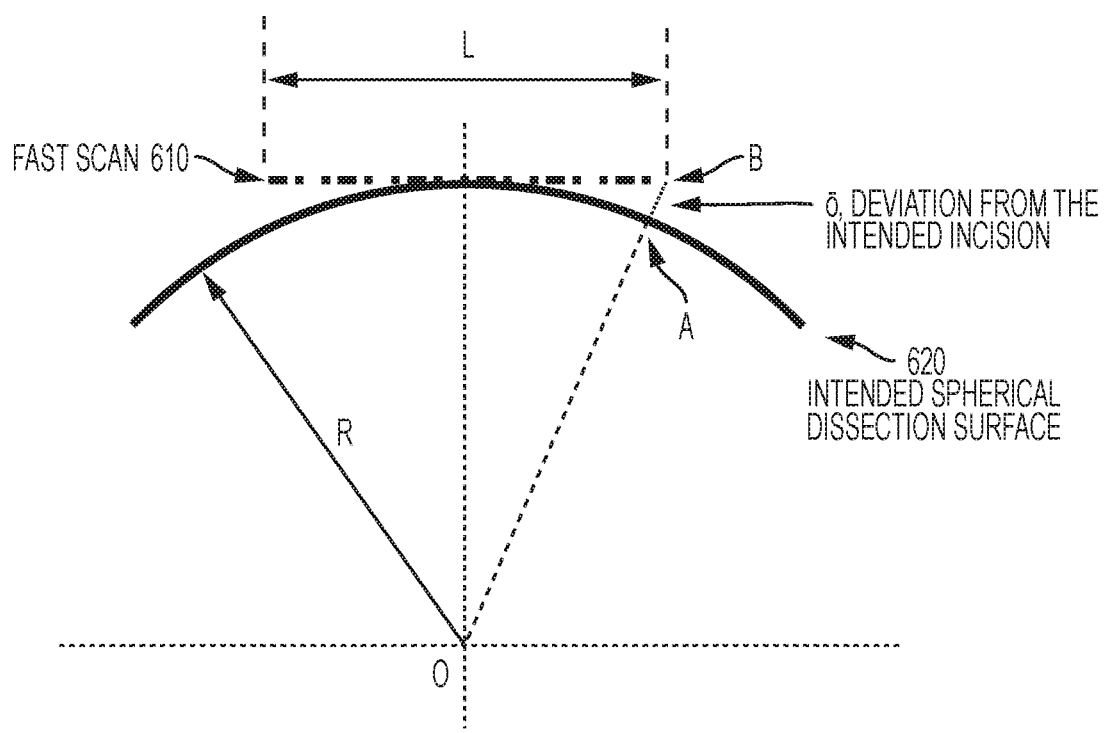
FIG. 6 illustrates a geometric relation between a fast-scan line and an intended spherical dissection surface of a surgical ophthalmic laser system according to an embodiment of the present invention.

FIG. 6 shows the geometric relation between the fast scan line 610 and the intended spherical dissection surface 620, e.g., of a lens, especially the distance deviation (δ) between the end point B of the scan line 620 and point A on the intended dissection surface 620. The maximum deviation δ is the distance between point A and point B, and is given by:

$$\delta = \sqrt{R^2 + \frac{L^2}{4}} - R = \frac{L^2}{8R} \qquad \text{Equation (1)}$$

where R is greater than L, R is the radius of curvature of the surface dissection 620, and L is the length of the fast scan.

Figure 7:
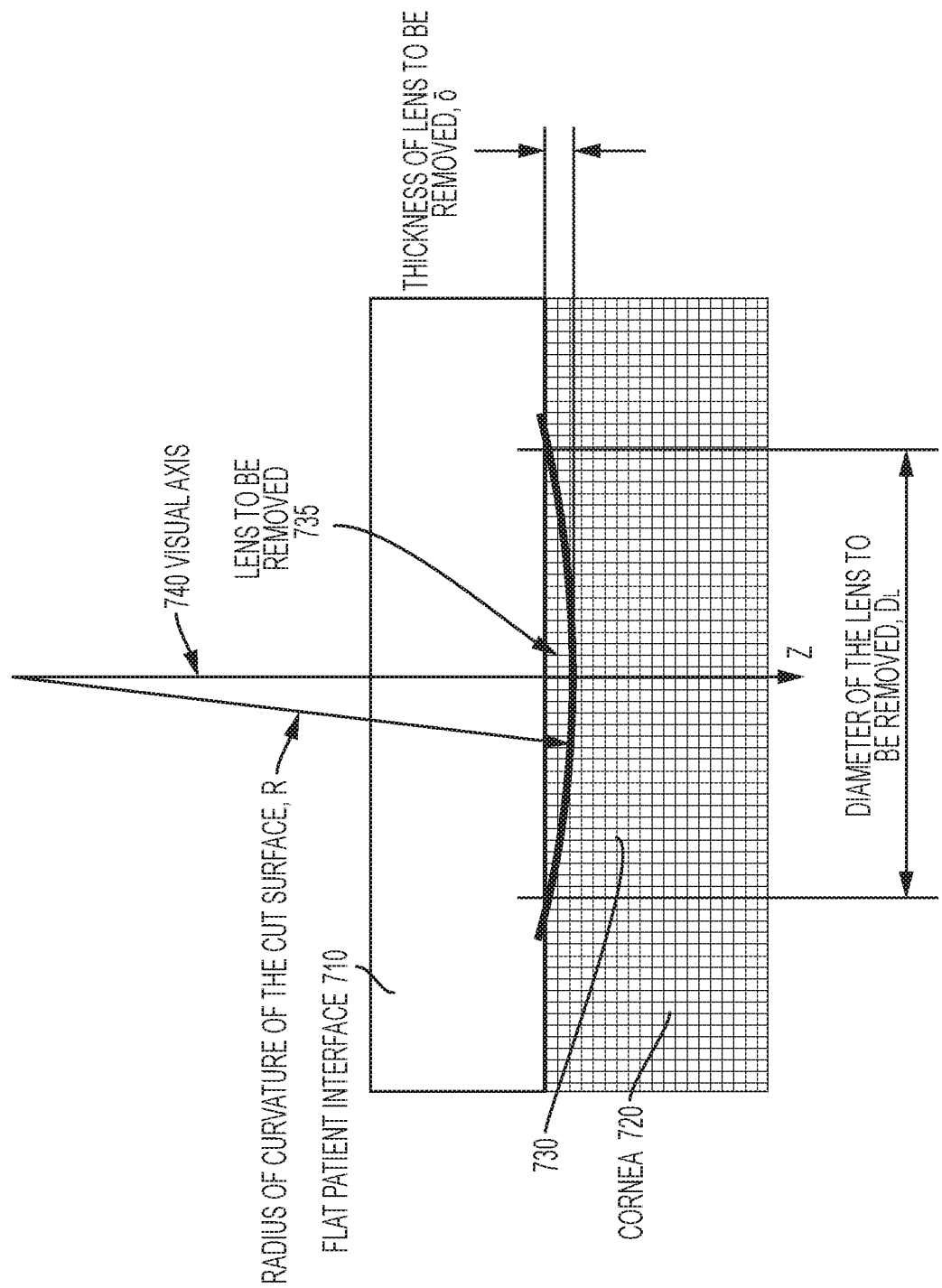
FIG. 7 illustrates an exemplary flat patient interface surface dissection using a surgical ophthalmic laser system according to an embodiment of the present invention.

FIG. 7 illustrates an exemplary flat patient interface surface dissection using a surgical ophthalmic laser system according to an embodiment of the present invention. A flat patient interface 710 is provided to flatten the cornea 720 and fix the patient eye to the system 10. The Z axis corresponds to a visual axis 740. Typically, a diameter of the lens $D_L$ to be removed is selected by a doctor and may be, for example, 6 mm. A cut surface 730 generated by the laser beam has a radius of curvature R and a lens thickness δ. The resultant lens 735 is the anterior surface volume dissected by the laser beam.

Let n (=1.377) be the refractive index of cornea, $D_L$ the diameter of the thin-lens to be removed and ΔD (positive) the value of desired myopia correction. Then, the radius of curvature of the cutting surface R, is approximately given by:

$$R = \frac{(n-1)}{\Delta D} \qquad \text{Equation (2)}$$

A positive value of R means that the center of the cut spherical surface is above the cut surface. The central thickness of the to-be-removed, thin-lens shape cornea tissue, is given by:

$$\delta \approx \frac{(\Delta D) \cdot D_L^2}{8(n-1)} \qquad \text{Equation (3)}$$

Considering a case where $D_L$=6 mm, ΔD=10 diopter, then R=37.7 mm and δ=119.4 μm. The specific shape of the cut surface may b further modified to correct for other types of aberrations that may be present.

To make a precision surface cut, the depth of focus (i.e., the Rayleigh range) of the femtosecond laser must be sufficiently small. For a Gaussian laser beam, the half-range of the depth of focus is given by the following formula:

$$\Delta = \frac{n \cdot \pi \cdot w^2}{\lambda} \quad \text{Equation (4)}$$

where $w$ is the $1/e^2$ radius of the focus spot, and $\lambda$ is the laser wavelength at vacuum. Equation (4) can also be written as Equation (5), using $w=K \cdot \lambda/(4NA)$, where NA is the numerical aperture, $K=11.83$ is a constant for a Gaussian beam truncated by an aperture at its $1/e^2$ intensity point:

$$\Delta = \frac{n \cdot \pi \cdot K^2 \cdot \lambda}{(4NA)^2} \approx \frac{0.905 \cdot \lambda}{(NA)^2} \quad \text{Equation (5)}$$

The actual thickness of the cutting zone depends on the depth of focus and also the laser pulse energy; the smaller the pulse energy, the shorter the thickness of the cutting zone. Since the pulse energy must be above the cutting threshold energy, the thickness cannot be made to be infinitely small just by lowering the pulse energy. The depth of focus not only affects the cutting zone thickness, but also the smoothness of the dissection surface which will affect both local refractive power and light scattering after the surgery. The depth of focus should be minimized for optimal results. However, a smaller depth of focus requires a bigger NA, increasing the difficulty and complexity of the optics. Considering a diopter of correction corresponds to about 12 μm tissue removal, the depth of focus A is preferably under 10 μm and more preferably under 6 μm.

Figure 8:
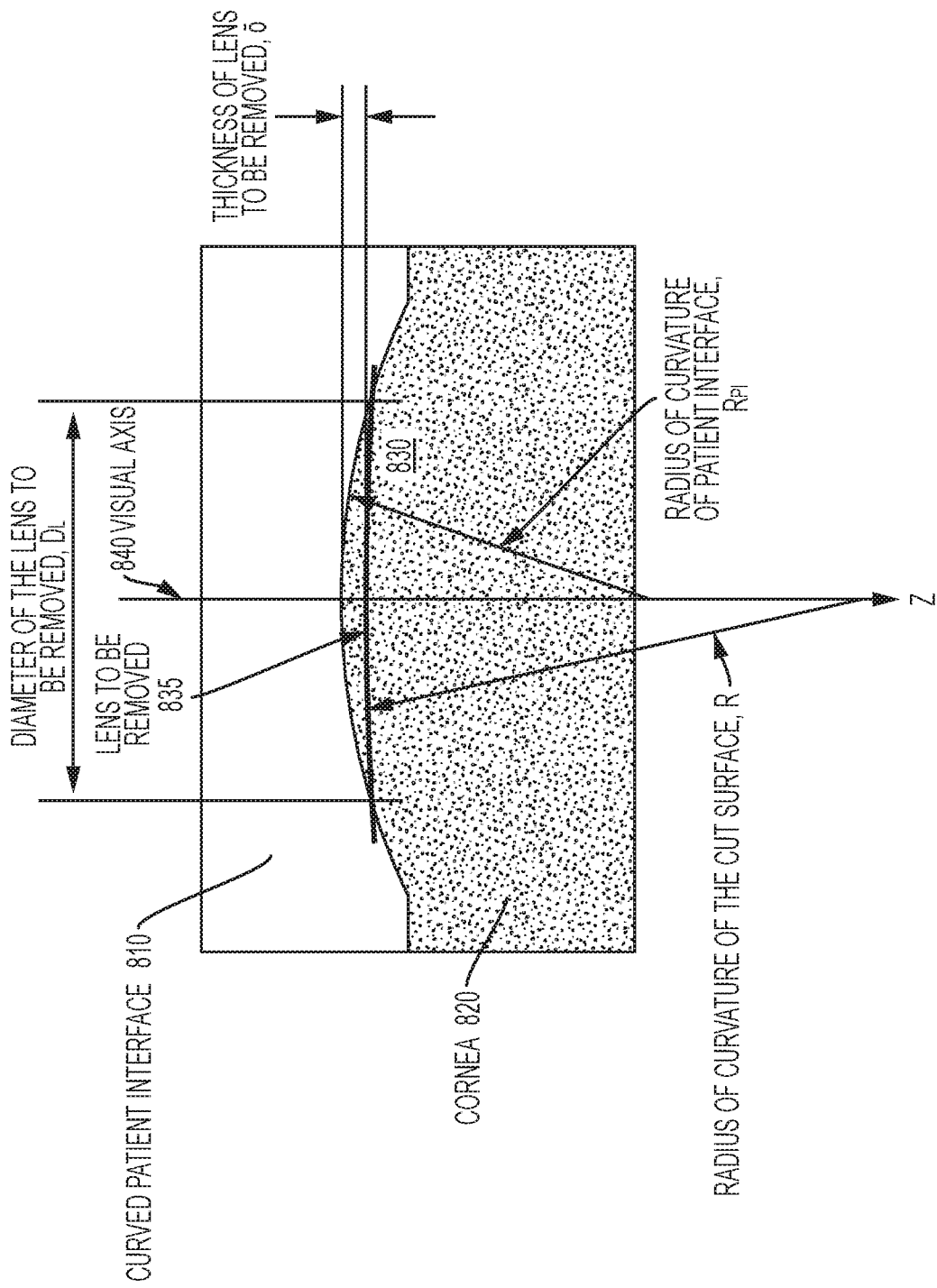
FIG. 8 illustrates an exemplary curved patient interface surface dissection using a surgical ophthalmic laser system according to an embodiment of the present invention.

FIG. 8 illustrates an exemplary curved patient interface surface dissection using a surgical ophthalmic laser system according to an embodiment of the present invention. A curved patient interface 810 is provided that contacts the cornea 820 to fix the patient eye to the system 10. The Z axis corresponds to a visual axis 840. Typically, a diameter of the lens $D_L$ to be removed is selected by a doctor and may be, for example, 6 mm. A cut surface 830 generated by the laser beam has a radius of curvature R and a lens thickness δ. A curved interface 810 has a radius of curvature $R_{PI}$. The resultant lens 835 is the anterior surface volume dissected by the laser beam.

Let $R_{PI}$ be the radius of curvature of the patient interface, then, similar to Equation (2), R is given by:

$$R = \left[\frac{1}{R_{PI}} - \frac{\Delta D}{(n-1)}\right]^{-1} \quad \text{Equation (6)}$$

For a flat patient interface, $R_{PI}=\infty$ and Equation (6) reduces to the form of Equation (2), except for a sign difference due to definition; for a curved patient interface, the positive radius of curvature R is defined such that the center of the sphere is below the cut surface. This sign selection is made for convenience as the radius of curvature of a curved patient interface is usually (e.g., less than 13 mm), and for myopia correction within 12 diopters, the dissection surface is curved like in FIG. 7.

The central thickness of the thin-lens 735, 835 to be removed, as given in Equation (3), does not depend on the shape of the patient interface. Accordingly, Equation (3) also applies to a curved patient interface. For instance, considering a curved patient interface with $R_{PI}=10$ mm, $\Delta D=10$ diopter, and $D_L=6$ mm, then $R=13.6$ mm and $\delta=119.4$ μm. The thicknesses δ of the lens to be removed for the curved and flat interfaces are the same.

Figure 9:
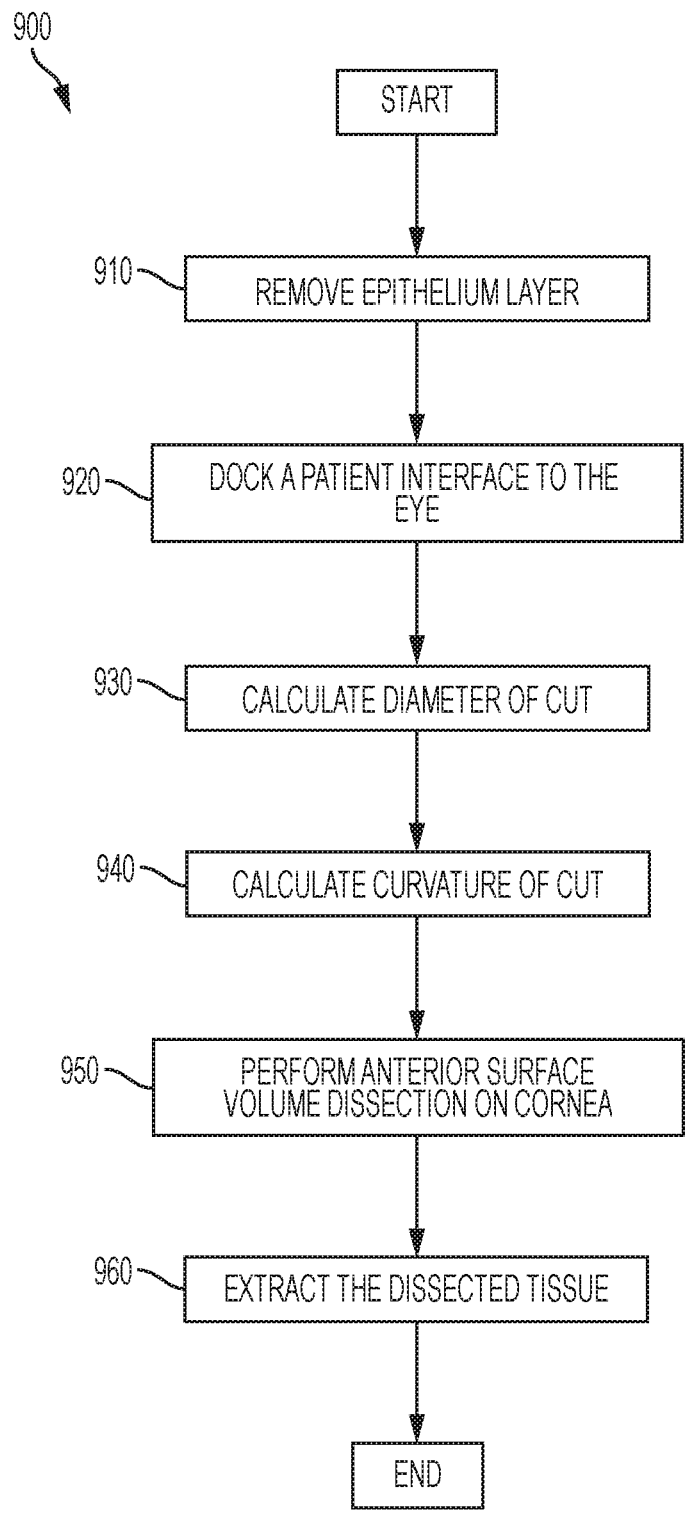
FIG. 9 is a flowchart illustrating an exemplary femtosecond laser PRK process according to an embodiment of the present invention.
Figure 10:
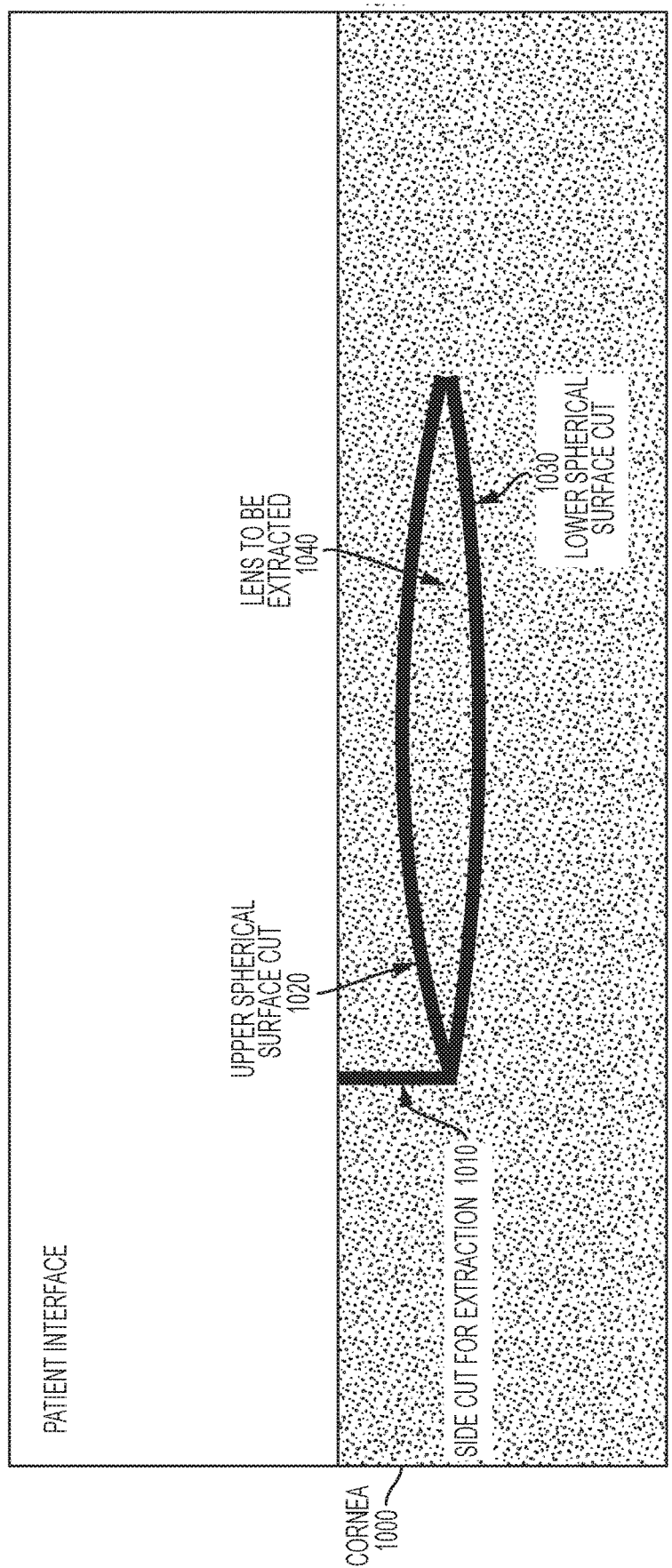
FIG. 10 is a cross-sectional view of a lenticular extraction using a surgical ophthalmic laser system according to the prior art.
Figure 11:
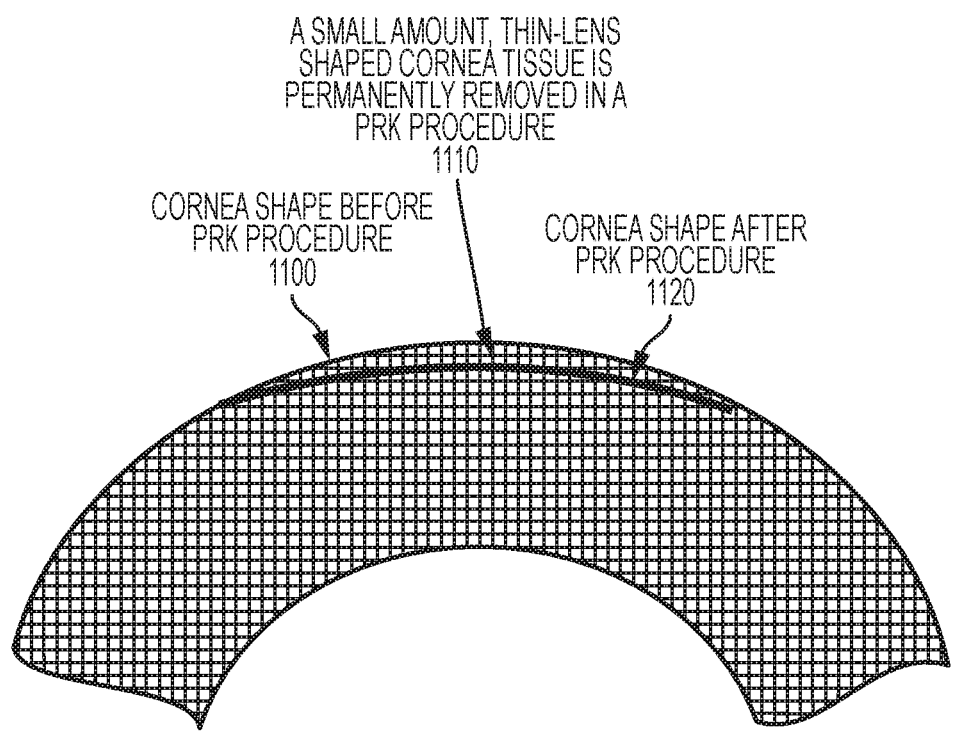
FIG. 11 is a cross-sectional view of a conventional PRK procedure using a surgical ophthalmic laser system according to the prior art.

The embodiments disclosed herein enable a PRK procedure using an ultra-short pulsed laser, such as a femtosecond laser. FIG. 9 illustrates a process 900 of the laser system 10 according to an embodiment. The procedure begins by removal of the epithelium layer of the cornea (Action Block 910). Then, the patient's eye is docked to a patient interface, so that the laser system and the eye form a fixed geometric configuration (Action Block 920). The patient interface of the system 10 couples to and constrains the eye relative to the laser delivery system. A surface of the patient interface in contact with the cornea is flat or curved. Alternatively, the patient interface may also contact and fix the cornea in position via a liquid interface.

Next, the laser system 10 determines the parameters of vision correction: in particular, the laser system 10 determines a diameter of the lens to be removed or receives cornea dissection parameters from a user (Action Block 930). The laser system 10 then determines the radius of curvature (Action Block 940) corresponding to the amount of correction, e.g., the myopic correction determined in pre-operation measurements, as shown, for example, in equations (2) and (6) above. The laser system 10 generates the femtosecond laser pulse beams controlled by a controller 52 to perform anterior surface volume dissection on the cornea based on the determined vision correction parameters (Action Block 950), The dissected anterior surface volume is then extracted and discarded (Action Block 960). The femtosecond laser dissects a thin-lens shaped volume of cornea stroma tissue at the anterior cornea. Once dissected, the whole piece of the thin-lens shaped cornea stroma tissue is discarded. It is noted that other types of corneal cuts such as relaxing incisions are not surface volume dissections since no material is removed. Laser ablation also does not produce a volume dissection. In addition to myopia correction, the methods and systems herein may be applied to embodiments for hyperopia correction, by reshaping the anterior cornea shape with a femtosecond laser. The methods and systems herein may be applied to embodiments for presbyopia correction, by creating a multi-focal thin-lens shape at the anterior cornea with a femtosecond laser. In other embodiments, the laser system 10 may also be used to produce other three-dimensional surface shapes, including toric surfaces for hyperopic and astigmatic corrections. The laser system 10 may also be used for laser material processing and micromachining for other transparent materials.

The systems and methods described above provide numerous advantages over conventional procedures and systems. For example, in conventional PRK procedures performed with an excimer laser, the tissue ablation rates can vary with the level of corneal hydration. This source of variation, however, does not affect femtosecond laser cutting depth, and the embodiments described herein provide more consistent outcomes for eyes with different levels of corneal hydration.

Furthermore, PRK performed with a femtosecond laser as a method for laser vision correction improves equipment use, and may reduce cost of acquiring and maintaining laser systems. For instance, current refractive surgery suites usually have a minimum of two expensive capital systems, including (1) an ultra-short pulsed laser, such as a femtosecond laser for cutting a corneal flap; and (2) an excimer laser for corneal ablation. The embodiments described herein, however, enable surgeons to acquire surgical refractive surgery suites that comprise of only one femtosecond laser system to perform both PRK as well as other refractive procedures like SmILE.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser source generating a pulsed laser beam;
   a laser delivery system delivering the pulsed laser beam to a cornea of an eye;
   a patient interface coupling to and constraining the eye relative to the laser delivery system, wherein a surface of the patient interface in contact with the cornea is curved; and
   a controller controlling the laser delivery system to perform an anterior surface volume dissection on the cornea by forming a cutting surface in the cornea that dissects a volume of cornea tissue that contains an anterior corneal surface, wherein a radius of curvature R of the cutting surface is:

$$R = \left[\frac{1}{R_{PI}} - \frac{\Delta D}{(n-1)}\right]^{-1}$$

where n is a refractive index of the cornea, $\Delta D$ a predetermined value of vision correction, and $R_{PI}$ is a radius of curvature of surface of the patient interface in contact with the cornea.

2. The ophthalmic surgical laser system of claim 1, wherein the laser source is a femtosecond laser.

3. The ophthalmic surgical laser system of claim 1, wherein the laser source is a UV light laser providing 355 nm laser light beam.

4. The ophthalmic surgical laser system of claim 1, wherein the laser delivery system scans the cornea by point-to-point scanning.

5. The ophthalmic surgical laser system of claim 1, wherein the laser delivery system scans the cornea by fast scan line scanning.

6. An ophthalmic surgical laser system comprising:
   a laser source generating a pulsed laser beam;
   a laser delivery system delivering the pulsed laser beam to a cornea of an eye;
   a patient interface coupling to and constraining the eye relative to the laser delivery system; and
   a controller controlling the laser delivery system to perform an anterior surface volume dissection on the cornea by forming a cutting surface in the cornea that dissects a volume of cornea tissue that contains an anterior corneal surface,
   wherein a depth of focus of the pulsed laser beam is under 10 μm and is given by:

$$\Delta = \frac{0.905 \cdot \lambda}{(NA)^2}$$

where $\Delta$ is the depth of focus in cornea, $\lambda$ is the laser wavelength, and NA is the numerical aperture of the focusing beam.

7. The ophthalmic surgical laser system of claim 6, wherein the laser source is a femtosecond laser.

8. The ophthalmic surgical laser system of claim 6, wherein the laser source is a UV light laser providing 355 nm laser light beam.

9. The ophthalmic surgical laser system of claim 6, wherein a surface of the patient interface in contact with the cornea is curved.

10. The ophthalmic surgical laser system of claim 6, wherein the laser delivery system scans the cornea by point-to-point scanning.

11. The ophthalmic surgical laser system of claim 6, wherein the laser delivery system scans the cornea by fast scan line scanning.

* * * * *